United States Patent
Prince (10) Patent No.: US 11,925,505 B2
(45) Date of Patent: Mar. 12, 2024

(54) MINIMUM CATHETER LENGTH TOOL

(71) Applicant: Bard Access Systems, Inc., Salt Lake City, UT (US)

(72) Inventor: Matthew J. Prince, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/485,035

(22) Filed: Sep. 24, 2021

(65) Prior Publication Data

US 2022/0096797 A1    Mar. 31, 2022

Related U.S. Application Data

(60) Provisional application No. 63/083,684, filed on Sep. 25, 2020.

(51) Int. Cl.
   *A61B 8/08*    (2006.01)
   *A61B 8/00*    (2006.01)

(52) U.S. Cl.
   CPC .............. *A61B 8/085* (2013.01); *A61B 8/465* (2013.01); *A61B 8/469* (2013.01); *A61B 8/4472* (2013.01)

(58) Field of Classification Search
   CPC ......... A61B 8/085; A61B 8/465; A61B 8/469; A61B 8/4472; A61B 8/0841; A61B 8/0891
   See application file for complete search history.

(56) References Cited

U.S. PATENT DOCUMENTS

| | | |
|---|---|---|
| 5,148,809 A | 9/1992 | Biegeleisen-Knight et al. |
| 5,181,513 A | 1/1993 | Touboul et al. |
| 5,325,293 A | 6/1994 | Dorne |
| 5,441,052 A | 8/1995 | Miyajima |
| 5,549,554 A | 8/1996 | Miraki |

(Continued)

FOREIGN PATENT DOCUMENTS

| | | |
|---|---|---|
| CN | 101854853 A | 10/2010 |
| CN | 105054962 A | 11/2015 |

(Continued)

OTHER PUBLICATIONS

PCT/US2022/034380 filed Jun. 21, 2022 International Search Report and Written Opinion dated Oct. 5, 2022.

(Continued)

*Primary Examiner* — Peter Luong (74) *Attorney, Agent, or Firm* — Rutan & Tucker LLP (57) ABSTRACT

An ultrasound imaging system includes an ultrasound probe designed to produce an ultrasound image including one or more blood vessels below a skin surface of a patient, and a console with a display. The console is operably coupled to the ultrasound probe. The console includes a memory including instructions capable of causing a processor to determine a depth of the user selected blood vessel and a selection of medical devices based on a user selection including one or both of a minimum dwell length and an angle of insertion. The processor can be configured to determine these parameters prior to insertion of a user selected medical device into a user selected blood vessel from the one or more blood vessels below the skin surface of the patient. The display depicts the ultrasound image, the user selected blood vessel, and the user selected medical device.

8 Claims, 8 Drawing Sheets

(56) References Cited

U.S. PATENT DOCUMENTS

| | | |
|---|---|---|
| 5,573,529 A | 11/1996 | Haak et al. |
| 5,775,322 A | 7/1998 | Silverstein et al. |
| 5,879,297 A | 3/1999 | Haynor et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,702,749 B2 | 3/2004 | Paladini et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,756,766 B2 | 9/2017 | Best |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 9,950,139 B2 | 4/2018 | Blanchard et al. |
| 10,043,272 B2 | 8/2018 | Forzoni et al. |
| 10,449,330 B2 | 10/2019 | Newman et al. |
| 10,524,691 B2 | 1/2020 | Newman et al. |
| 10,751,509 B2 | 8/2020 | Misener |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0004290 A1 | 1/2006 | Smith et al. |
| 2006/0013523 A1 | 1/2006 | Childlers et al. |
| 2006/0015039 A1 | 1/2006 | Cassidy et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0161687 A1 | 7/2008 | Suri et al. |

(56) References Cited

U.S. PATENT DOCUMENTS

| | | |
|---|---|---|
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0182224 A1 | 7/2009 | Shmarak et al. |
| 2009/0306509 A1 | 12/2009 | Pedersen et al. |
| 2010/0211026 A2 | 8/2010 | Sheetz et al. |
| 2010/0286515 A1 | 11/2010 | Gravenstein et al. |
| 2010/0305442 A1* | 12/2010 | Tierney ............... A61B 8/12 714/E11.029 |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0313293 A1 | 12/2011 | Lindekugel et al. |
| 2012/0078103 A1 | 3/2012 | Tashiro et al. |
| 2012/0165679 A1 | 6/2012 | Orome et al. |
| 2012/0179038 A1 | 7/2012 | Meurer et al. |
| 2012/0197132 A1 | 8/2012 | O'Connor |
| 2012/0220865 A1 | 8/2012 | Brown et al. |
| 2012/0253200 A1 | 10/2012 | Stolka et al. |
| 2012/0277576 A1 | 11/2012 | Lui |
| 2013/0006102 A1 | 1/2013 | Wilkes et al. |
| 2013/0041250 A1 | 2/2013 | Pelissier et al. |
| 2013/0102889 A1* | 4/2013 | Southard ............ C08G 61/125 600/424 |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2013/0261553 A1 | 10/2013 | Sheldon et al. |
| 2014/0005530 A1 | 1/2014 | Liu et al. |
| 2014/0073976 A1 | 3/2014 | Fonte et al. |
| 2014/0100440 A1 | 4/2014 | Cheline et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0275997 A1 | 9/2014 | Chopra et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0148668 A1 | 5/2015 | Stolka et al. |
| 2015/0209113 A1 | 7/2015 | Burkholz et al. |
| 2015/0209526 A1 | 7/2015 | Matsubara et al. |
| 2015/0216442 A1 | 8/2015 | Lavy et al. |
| 2015/0272553 A1 | 10/2015 | Thattari Kandiyil et al. |
| 2015/0297097 A1 | 10/2015 | Matsubara et al. |
| 2015/0320325 A1 | 11/2015 | Sheehan et al. |
| 2015/0359991 A1 | 12/2015 | Dunbar et al. |
| 2016/0029995 A1 | 2/2016 | Navratil et al. |
| 2016/0113699 A1 | 4/2016 | Sverdlik et al. |
| 2016/0120607 A1 | 5/2016 | Sorotzkin et al. |
| 2016/0128719 A1 | 5/2016 | Cermak |
| 2016/0166232 A1 | 6/2016 | Merritt |
| 2016/0202053 A1 | 7/2016 | Walker et al. |
| 2016/0213398 A1 | 7/2016 | Liu |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0056062 A1 | 3/2017 | Buljubasic |
| 2017/0079548 A1 | 3/2017 | Silverstein et al. |
| 2017/0079551 A1 | 3/2017 | Henkel et al. |
| 2017/0164923 A1 | 6/2017 | Matsumoto |
| 2017/0215842 A1 | 8/2017 | Ryu et al. |
| 2017/0290563 A1 | 10/2017 | Cole et al. |
| 2017/0367678 A1 | 12/2017 | Sirtori et al. |
| 2018/0015256 A1 | 1/2018 | Southard et al. |
| 2018/0061546 A1 | 3/2018 | Ma et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0289929 A1 | 10/2018 | Ma et al. |
| 2018/0310955 A1 | 11/2018 | Lindekugel et al. |
| 2019/0365348 A1 | 12/2019 | Toume et al. |
| 2020/0113540 A1 | 4/2020 | Gijsbers et al. |
| 2020/0230391 A1 | 7/2020 | Burkholz et al. |
| 2020/0245969 A1 | 8/2020 | Tung et al. |
| 2020/0315592 A1* | 10/2020 | Soleimani ............ A61B 8/4427 |
| 2020/0359990 A1 | 11/2020 | Poland et al. |
| 2021/0015448 A1 | 1/2021 | Sokulin et al. |
| 2021/0045717 A1 | 2/2021 | Schwab |
| 2021/0059636 A1 | 3/2021 | Durfee et al. |
| 2021/0085282 A1 | 3/2021 | Prince |
| 2021/0169585 A1 | 6/2021 | Prince et al. |
| 2021/0186456 A1 | 6/2021 | Prince |
| 2021/0275256 A1 | 9/2021 | Sowards et al. |
| 2022/0022969 A1 | 1/2022 | Misener |
| 2022/0039685 A1 | 2/2022 | Misener et al. |
| 2022/0039777 A1 | 2/2022 | Durfee |
| 2022/0101980 A1 | 3/2022 | Rothenberg et al. |
| 2022/0104886 A1 | 4/2022 | Blanchard et al. |
| 2022/0117582 A1 | 4/2022 | McLaughlin et al. |
| 2022/0142608 A1 | 5/2022 | Matsumoto |
| 2022/0160434 A1 | 5/2022 | Messerly et al. |
| 2022/0280246 A1 | 9/2022 | Messerly et al. |
| 2022/0304652 A1 | 9/2022 | Peterson et al. |
| 2022/0401157 A1 | 12/2022 | Sowards et al. |
| 2023/0121370 A1 | 4/2023 | Sowards et al. |
| 2023/0147164 A1 | 5/2023 | Sowards et al. |
| 2023/0148993 A1 | 5/2023 | Sowards et al. |
| 2023/0329748 A1 | 10/2023 | Sowards et al. |
| 2023/0338003 A1 | 10/2023 | Misener et al. |

FOREIGN PATENT DOCUMENTS

| | | |
|---|---|---|
| CN | 216167530 U | 4/2022 |
| EP | 0933063 A1 | 8/1999 |
| EP | 1504713 A1 | 2/2005 |
| EP | 0788329 B1 | 12/2006 |
| EP | 1591074 B1 | 5/2008 |
| EP | 3181083 A1 | 6/2017 |
| JP | 2000271136 A | 10/2000 |
| JP | 2018175547 A | 11/2018 |
| KR | 20180070878 A | 6/2018 |
| WO | 2013059714 A1 | 4/2013 |
| WO | 2014/115150 A1 | 7/2014 |
| WO | 2015/017270 A1 | 2/2015 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020/186198 A1 | 9/2020 |
| WO | 2021113733 A1 | 6/2021 |
| WO | 2022/067101 A1 | 3/2022 |
| WO | 2022/072727 A2 | 4/2022 |
| WO | 2022/081904 A1 | 4/2022 |
| WO | 2022/150411 A1 | 7/2022 |
| WO | 2022/187701 A1 | 9/2022 |
| WO | 2022212414 A1 | 10/2022 |
| WO | 2022/271728 A1 | 12/2022 |
| WO | 2023064492 A1 | 4/2023 |

(56) References Cited

FOREIGN PATENT DOCUMENTS

| WO | 2023081414 A1 | 5/2023 |
| WO | 20023091427 A1 | 5/2023 |

OTHER PUBLICATIONS

PCT/US2022/046606 filed Oct. 13, 2022 International Search Report and Written Opinion dated Feb. 6, 2023.
PCT/US2022/049042 filed Nov. 4, 2022 International Search Report and Written Opinion dated Mar. 1, 2023.
PCT/US2022/049989 filed Nov. 15, 2022 International Search Report and Written Opinion dated Feb. 6, 2023.
U.S. Appl. No. 17/112,735, filed Dec. 4, 2022 Non-Final Office Action dated Oct. 26, 2022.
PCT/US12/61182 International Seach Report and Written Opinion dated Mar. 11, 2013.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
Murphy, Ethan K., et al., "Phantom Studies of Fused-Data TREIT Using Only Biopsy-Probe Electrodes" IEEE Transactions on Medical Imaging, IEEE, USA. vol. 39 No. 114, May 2020. (May 4, 2020).
PCT/US2020/063441 filed Dec. 4, 2020 International Preliminary Report on Patentability dated May 17, 2022.
PCT/US2022/019017 filed Mar. 4, 2022 International Search Report and Written Opinion dated Jun. 14, 2022.
PCT/US2022/022400 filed Mar. 29, 2022 International Search Report and Written Opinion dated Jul. 8, 2022.
PCT/US2021/045218 filed Aug. 9, 2021 International Search Report and Written Opinion dated Nov. 23, 2021.
PCT/US2021/049123 filed Sep. 3, 2021 International Search Report and Written Opinion dated Feb. 4, 2022.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.
U.S. Appl. No. 17/020,476, filed Sep. 14, 2020 Non-Final Office Action dated Feb. 9, 2022.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
PCT/US2020/063441 filed Dec. 4, 2020 International Search Report and Written Opinion dated Mar. 19, 2021.
U.S. Appl. No. 15/951,903, filed Apr. 12, 2018 Board Decision dated Apr. 20, 2022.
U.S. Appl. No. 15/951,903, filed Apr. 12, 2018 Notice of Allowance dated May 2, 2022.
PCT/US2023/018680 filed Apr. 14, 2023 International Seach Report and Written Opinion dated Aug. 11, 2013.
PCT/US2023/023616 filed May 25, 2023 International Search Report and Written Opinion dated Aug. 16, 2023.
PCT/US2023/025259 filed Jun. 14, 2023 International Search Report and Written Opinion dated Sep. 25, 2023.
PCT/US2023/025845 filed Jun. 21, 2023 International Search Report and Written Opinion dated Sep. 26, 2023.
PCT/US2023/027042 filed Jul. 6, 2023 International Search Report and Written Opinion dated Oct. 10, 2023.
Schmidt G A et al Ultrasound-guided 1-22 vascular access in critical illness Intensive Care Medicine Springer Berlin Heidelberg Berlin/Heidelberg vol. 45 No. 4 Feb. 18, 2019 Feb. 18, 2019 pp. 434-446 XP036747615 ISSN 0342-4642 DOI 10.1007/S00134-019-05564-7 retrieved on Feb. 18, 2019.
U.S. Appl. No. 17/707,662, filed Mar. 29, 2022 Non-Final Office Action dated Oct. 17, 2023.
U.S. Appl. No. 17/725,370, filed Apr. 20, 2022 Non-Final Office Action dated Aug. 4, 2023.
Beigi, P. et al., "Enhancement of needle visualization and localization in ultrasound." International Journal of Computer Assisted Radiology and Surgery, vol. 16, No. 130, Sep. 2020 [Sep. 30, 2020] pp. 169-178.
PCT/US2023/018340 filed Apr. 12, 2023 International Seach Report and Written Opinion dated Jul. 20, 2023.
U.S. Appl. No. 17/112,725, filed Dec. 4, 2020 Final Office Action dated Apr. 14, 2023.
U.S. Appl. No. 17/725,370, filed Apr. 20, 2022 Restriction Requirement dated Apr. 27, 2023.

* cited by examiner

MINIMUM CATHETER LENGTH TOOL

PRIORITY

This application claims the benefit of priority to U.S. Provisional Application No. 63/083,684, filed Sep. 25, 2020, which is incorporated by reference in its entirety into this application.

BACKGROUND

When placing a vascular access device, clinicians must select a catheter based upon a number of different parameters. Current systems can force clinicians to select a vascular access device ("VAD") first, then use software and ultrasound imaging to evaluate if the vascular access device they selected would be appropriate. However, the clinicians initial guess of vascular access device during pre-assessment may be incorrect, leaving clinicians to repeatedly guess until they finally arrive at the correct VAD. As such, clinicians would have to cycle through a selection of vascular access devices, evaluate the parameters of each VAD and use ultrasound imaging to confirm the VAD the clinicians selected would be the most appropriate for the target blood vessel. It would be beneficial to the patient, as well as time effective, for a tool that allows the clinicians to select a parameter (e.g., minimum catheter length in the vessel), image a vessel, display the vascular access device options that are most suitable and evaluate the vascular access device options in real time using ultrasound imaging. Disclosed herein is a system and method of use that addresses the foregoing.

Disclosed herein is a method for selecting a vascular access device for accessing a target blood vessel, including imaging one or more blood vessels, entering one or more parameter inputs including a minimum catheter dwell length or an angle of insertion, into a vascular access device selection tool, selecting a target blood vessel from the one or more blood vessels, determining a depth of the target blood vessel, and providing a selection of vascular access devices that are able to access the target blood vessel based on the one or more parameter inputs.

In some embodiments, the method includes using an ultrasound imaging system including a console communicatively coupled to an ultrasound probe and a display.

In some embodiments, the method includes where the vascular access device selection tool includes a parameter logic that is receiving the one or more parameter inputs from a user.

In some embodiments, the method includes where the vascular access device selection tool includes a target vessel selector logic that is determining a depth of the target blood vessel.

In some embodiments, the method includes where the vascular access device selection tool includes a catheter selection logic that is providing a selection of catheters capable of accessing the target blood vessel.

In some embodiments, the method includes where the vascular access device selection tool includes a minimum catheter length logic that is determining a selection of catheters that are capable of accessing the target blood vessel, based on the parameter.

In some embodiments, the method includes where the vascular access device selection tool includes a data store that is storing a selection of catheters including information about each catheter length.

In some embodiments, the method includes where the vascular access device selection tool includes a communications logic that is updating the selection of catheters from a remote computing device.

In some embodiments, the method includes where the vascular access device selection tool includes an ultrasound imaging logic that is receiving input from an ultrasound probe and depicting one or more ultrasound images on a display.

In some embodiments, providing a selection of vascular access devices includes selecting a vascular access device to use, on a display.

In some embodiments, providing a selection of vascular access devices further includes depicting the ultrasound image overlay of the selected vascular access device in the target blood vessel on the display.

Also disclosed herein is an ultrasound imaging system including a console communicatively coupled to an ultrasound probe and a display, the console having a processor and a vascular access device selection tool configured to receive one or more of a minimum catheter dwell length parameter input or an angle of insertion parameter input.

In some embodiments, the ultrasound imaging system includes where the vascular access device selection tool includes one or more logic modules coupled to memory including a parameter logic, configured to receive the one or more minimum catheter dwell length parameter input or angle of insertion parameter input from a user, a target vessel selector logic, configured to determine a depth of the target vessel and a catheter selection logic, configured to provide a selection of catheters capable of accessing the target vessel.

In some embodiments, the ultrasound imaging system includes where the vascular access device selection tool includes a minimum catheter dwell length logic, configured to determine catheters that are capable of accessing the target vessel, given the one or more minimum catheter dwell length parameter input or the angle of insertion parameter input from the user.

In some embodiments, the ultrasound imaging system includes where the vascular access device selection tool includes a data store, configured to store a list of catheters including information about each catheter length.

In some embodiments, the ultrasound imaging system includes where the vascular access device selection tool further includes a communications logic, configured to update the selection of catheters from a remote computing device.

In some embodiments, the ultrasound imaging system includes where the vascular access device selection tool includes an ultrasound imaging logic, configured to receive an input transmitted from the ultrasound probe and provide an ultrasound image.

In some embodiments, the ultrasound imaging system includes where the display is wirelessly coupled to the console.

In some embodiments, the ultrasound imaging system includes where the display is touch screen.

Also disclosed herein is a vascular access device selection tool including one or more logic modules coupled to memory including a parameter logic, configured to receive one or more parameter inputs from a user, a target vessel selector logic, configured to determine a depth of a target blood vessel, and a catheter selection logic, configured to provide a selection of catheters capable of accessing the target vessel. The vascular access device selection tool includes a minimum catheter dwell length logic, configured to determine catheters that are capable of accessing the target blood vessel, given the one or more parameter inputs from the user, a data store, configured to store a selection of catheters including information about each catheter, a communications logic, configured to update the selection of catheters, and an ultrasound imaging logic, configured to depict one or more ultrasound images on a display.

In some embodiments, the vascular access device selection tool includes the one or more parameter inputs including a minimum catheter dwell length, angle of insertion or a combination of the minimum catheter dwell length and the angle of insertion.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

As used herein a "vascular access device" can include a catheter, peripherally inserted central catheter ("PICC"), peripheral intravenous line ("PIV"), central venous catheter ("CVC"), midline catheter, or the like etc.

Unless defined otherwise, all technical and scientific terms used herein have the same meaning as commonly understood by those of ordinary skill in the art.

Figure 1A:
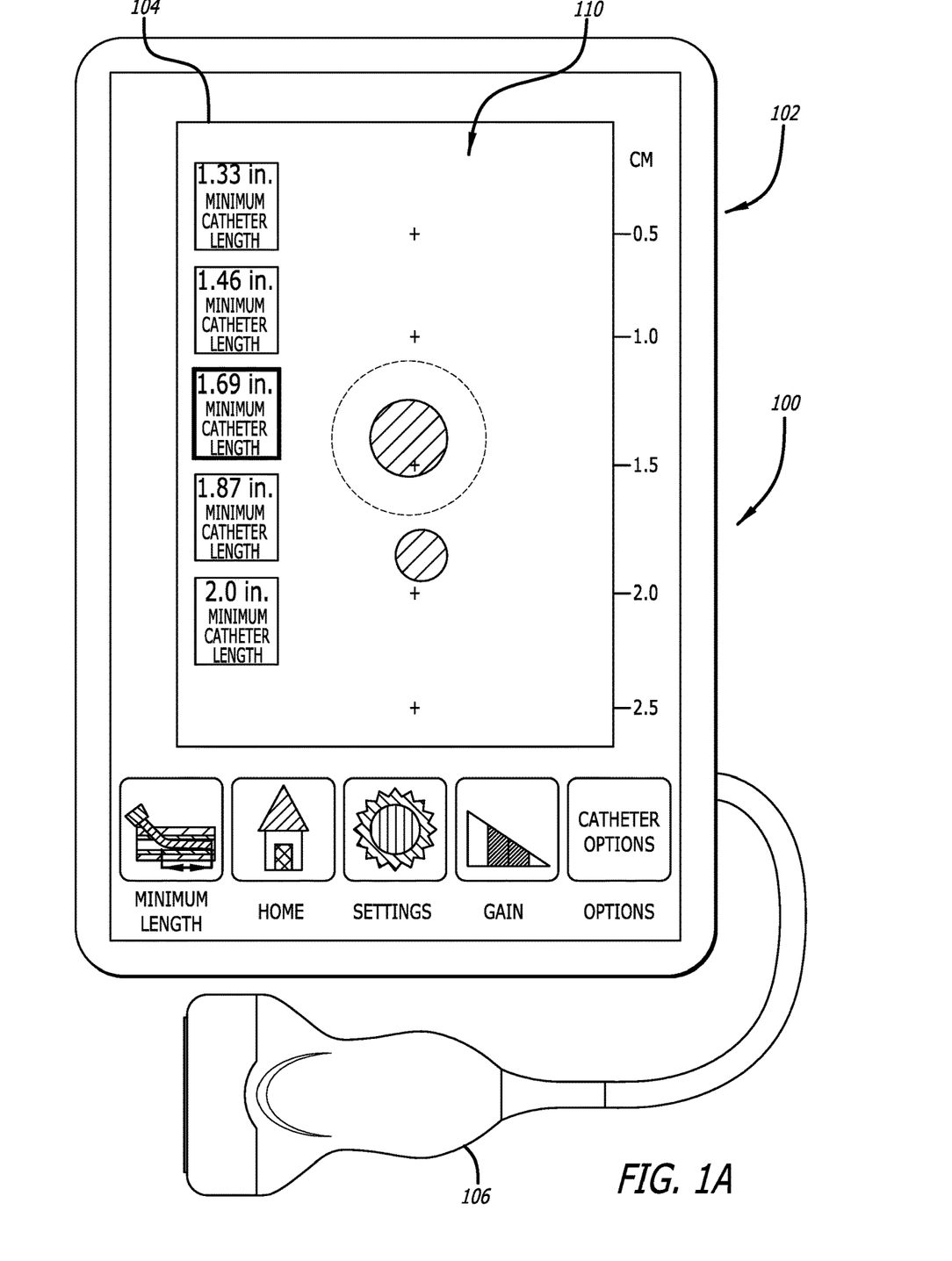
FIG. 1A illustrates a perspective view of an ultrasound imaging system including a minimum catheter length tool, in accordance with some embodiments.

FIG. 1A illustrates a perspective view of an ultrasound imaging system including a minimum catheter length tool, in accordance with some embodiments. In some embodiments, the ultrasound imaging system 100 includes an ultrasound probe 106 coupled to a console 102. In some embodiments, the ultrasound probe 106 may be wired to the console 102 or in wirelessly communication with the console 102. The ultrasound probe 106 may include transducer components for transmitting and receiving ultrasound signals that are transmitted to the console 102. In some embodiments, the ultrasound imaging system 100 includes the console 102 coupled to a display 104. In some embodiments, the console 102 may transmit ultrasound images to depict on the display 104. In some embodiments, the display 104 may be a touch screen. In some embodiments, the display 104 may be wired, or in wirelessly communication with the console 102. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like.

In some embodiments, the ultrasound imaging system 100 includes a minimum catheter length tool ("tool") 110 that may be configured to determine a selection of catheters that may achieve a minimum catheter dwell length based on the depth of a target vessel. As used herein, the minimum catheter dwell length is the length of a portion of a catheter that resides within the target vessel. The tool 110 can identify and depict on the display 104, all the potential catheters that fit the minimum catheter dwell length criteria for the given target vessel. The clinician can evaluate each potential catheter using the ultrasound imaging system 100 and chose a catheter, taking into account the results of the tool 110 along with other factors. When choosing a catheter, clinicians must evaluate a target vessel's depth, the desired minimum catheter dwell length in the target vessel, the overall catheter length, and the preferred angle of insertion of the catheter into the target vessel among other factors.

Figure 1B:
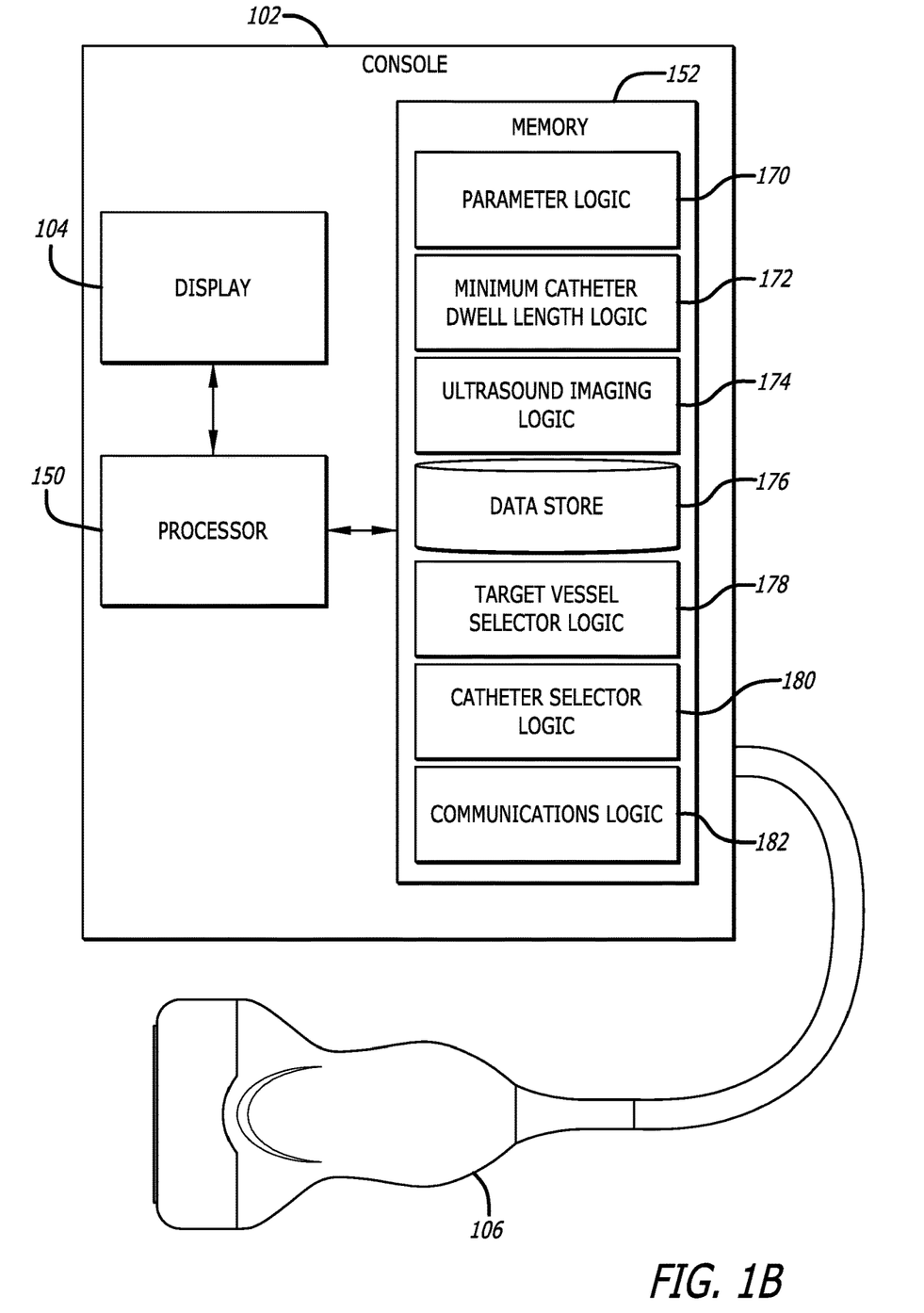
FIG. 1B illustrates a block diagram depicting various components of an ultrasound imaging system including a minimum catheter length tool, in accordance with some embodiments.

FIG. 1B illustrates a block diagram depicting various components of an ultrasound imaging system including a minimum catheter length tool, in accordance with some embodiments. In some embodiments, the console 102 may include various components necessary for receiving, displaying and analyzing ultrasound images of the target blood vessel from the probe 106. In some embodiments, the various components may include processor 150 and one or more logic modules coupled to memory 152 configured to perform at least one of the following: receive one or more parameter inputs from the user, calculate depth of a target blood vessel, provide a selection of catheters capable of accessing the target blood vessel, display one or more ultrasound images, determine catheters that are capable of accessing the target blood vessel given the user input, measure blood vessel area and blood vessel diameter, combinations thereof, or the like.

In some embodiments, the one or more logic modules may include a parameter logic 170, a minimum catheter dwell length logic 172, an ultrasound imaging logic 174, a data store 176, a target vessel selector logic 178, a catheter selector logic 180, a communications logic 182 or the like. In some embodiments, the parameter logic 170 may be configured to receive one or more parameter inputs (e.g., angle of insertion, desired minimum catheter dwell length in the blood vessel, or the like) from a user. In some embodiments, the minimum catheter dwell length logic 172 may be configured to determine a selection of catheters that are capable of accessing the target vessel, given the user input.

In some embodiments, the ultrasound imaging logic 174 may be configured to depict one or more ultrasound images on the display 104. In some embodiments, the data store 176 may be configured to store one or more of: the ultrasound image data, catheters that are capable of accessing the target vessel data, user input data, a selection of all catheters including information about each catheter, or the like. In some embodiments, the target vessel selector logic 178 may be configured to calculate the target blood vessel depth from a skin surface. In some embodiments, the catheter selection logic 180 may be configured to provide a selection of catheters that are capable of accessing the target blood vessel. In some embodiments, the communications logic 182 may be configured to update the selection of catheters from a remote computing device. In some embodiments, a remove computing device may include a cloud network, an internet network, an intranet network, a server network or the like.

The minimum catheter length tool 110 can allow a clinician to select one or more target blood vessels using the ultrasound imaging system 100, and provide the clinician a selection of suitable catheters to choose from, that meet various parameters including angle of insertion or minimum catheter dwell length, for the procedure. This contrasts with previous systems that require the clinician to choose a catheter first, then can advise if it is suitable, i.e. meets the minimum catheter dwell length requirement. Advantageously, the minimum catheter length tool 110 avoids the clinician guessing as to which catheters might be suitable, and instead provides a selection of catheters that will be suitable.

The minimum catheter length tool 110 requires one or more parameter inputs provided by the user, the console 102 or a combination thereof. The one or more inputs can include parameter inputs including minimum catheter dwell length, catheter length, angle of insertion, depth of a target vessel, units of measurement or the like. In some embodiments, the one or more parameter inputs can be entered into the minimum catheter length tool 110 either qualitatively or quantitatively, or a combination thereof. As used herein, quantitative information can include entering numerical values, optionally within a range of predetermined values, or the like. As used herein, qualitative information can include selections of predetermined values, groupings, or the like.

Figure 2A:
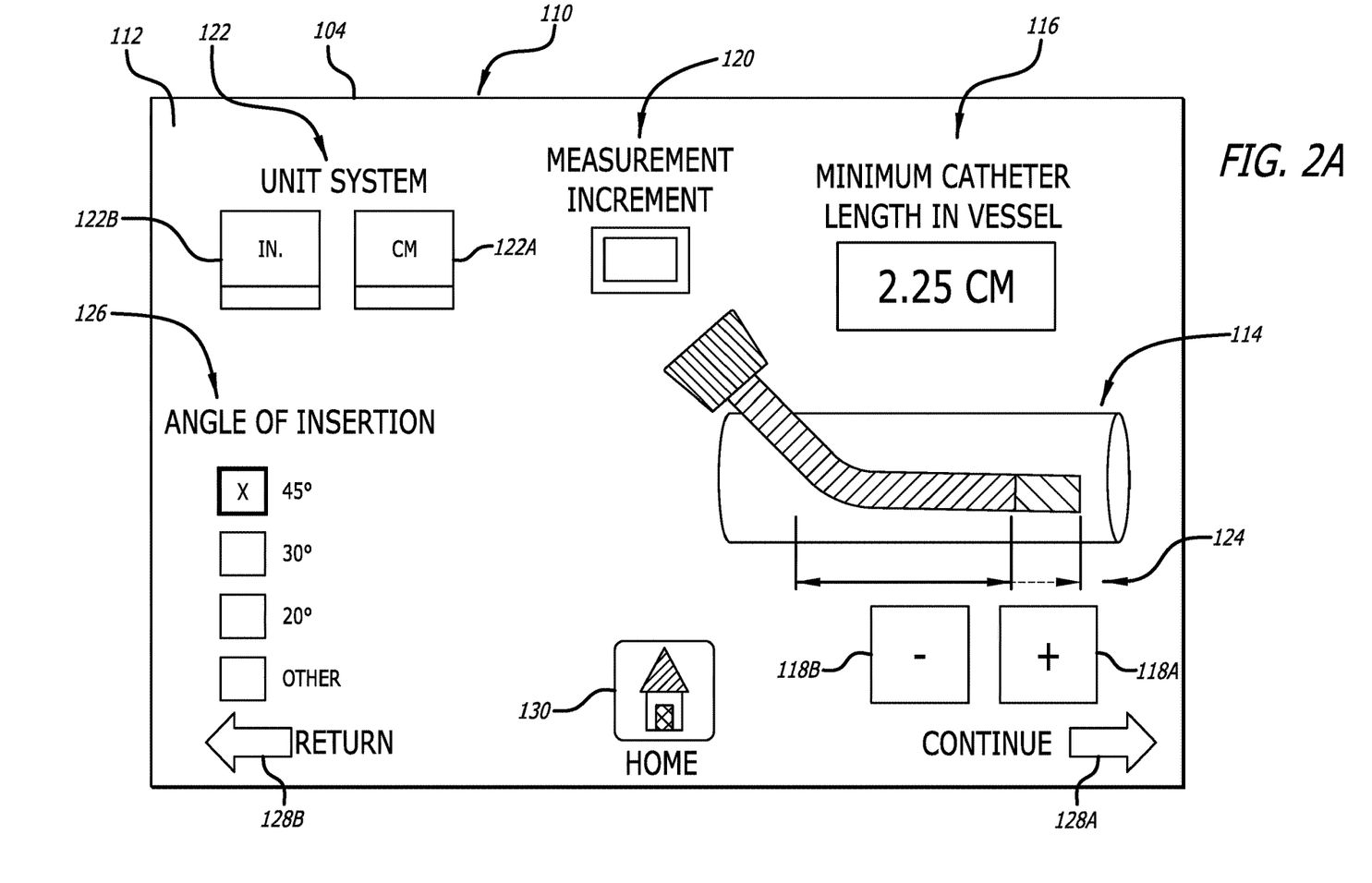
FIG. 2A illustrates an exemplary parameter input screen of the minimum catheter length tool, in accordance with some embodiments.

FIG. 2A illustrates an exemplary parameter input screen of the minimum catheter length tool 110, in accordance with some embodiments. In some embodiments, the minimum catheter length tool 110 can include a minimum catheter length tool parameter input screen ("parameter input screen") 112 that depicts a plurality of icons on the display 104. In some embodiments, the parameter input screen 112 can depict a catheter in a blood vessel icon 114. In some embodiments, the icon 114 can include an indicator icon 116 that corresponds to the specified minimum catheter dwell length, in units of measurement, of a catheter in the blood vessel. The indicator icon 116 may be configured to be changed to match the user's desired minimum catheter dwell length. In an embodiment, the minimum catheter dwell length can be selected by the clinician and entered to the tool 110 by way of the parameter input screen 112. In an embodiment, the minimum catheter dwell length can be predetermined by the tool 110.

In an embodiment, the clinician can adjust the minimum catheter dwell length. The indicator icon 116 may be configured to be increased or decreased by a standard unit of measurement with a positive icon 118A or a negative icon 118B. For example, selecting the positive icon 118A will increase the dwell length of the catheter in the blood vessel icon 114 while selecting the negative icon 118B will decrease the dwell length of the catheter in the blood vessel icon 114. The standard unit of measure may be modified by the user by selecting a measurement increment icon 120. The measurement increment icon 120 may be configured to allow the user to change the standard increment of the unit of measure depicted on the display 104. For example, the unit of measure increment may be 0.5 in. and the user can change the unit of measure increment to be 1.0 in, 0.1 in., 0.01 in. or the like. However, it will be appreciated that greater or lesser increments are also contemplated.

In some embodiments, the parameter input screen 112 includes a unit system icon 122 that allows a user to select between imperial or metric measurement systems of the indicator icon 116. In some embodiments, the user may select the desired units of measure displayed for the indicator icon 116. For example, the indicator icon 116 may be configured to be displayed in metric by selecting the centimeter unit of the unit system icon 122A. However, the user may select the inches unit of the unit system icon 122B which would display the indicator icon 116 in imperial units. In some embodiments, the unit system icon 122 may be configured to change the unit of measurement displayed on all user interfaces on the display 104.

In some embodiments, the icon 114 can further include a catheter dwell length icon 124 indicating, e.g. by an arrow or similar graphical representation, the dwell length of the catheter in the blood vessel. In some embodiments, as the indicator icon 116 is increased or decreased by the positive icon 118A or the negative icon 118B, the catheter dwell length icon 124 may be modified to correspondingly increase or decrease in displayed length.

The parameter input screen 112 may include an angle of insertion selection panel 126 that includes a selection of predetermined angles of insertion, for example "45°", "30°", "20°" or the like. However, it will be appreciated that other predetermined angles are also contemplated. In an embodiment, the user can select a specified angle of insertion by selecting "other" and entering an angle of insertion. Optionally, the angle of insertion entered by the user may be limited to a predetermined range. As used herein, the angle of insertion can be defined as angle of the catheter relative to a surface of a patient's skin at the point of insertion. In some embodiments, the "other" option may be configured to allow the user to specify the angle of insertion if the angle is not listed on the angle of insertion selection panel 126.

In some embodiments, the parameter input screen 112 includes one or more arrow icons 128A/B to help a user navigate through the user interface of the minimum catheter length tool 110. In some embodiments, the one or more arrow icons 128A/B can be indicated by text that includes "continue" or "return". In some embodiments, the parameter input screen 112 may include a home icon 130 configured to return the user to a home screen, navigation page, a displayed ultrasound image screen 200, or the like.

Figure 2B:
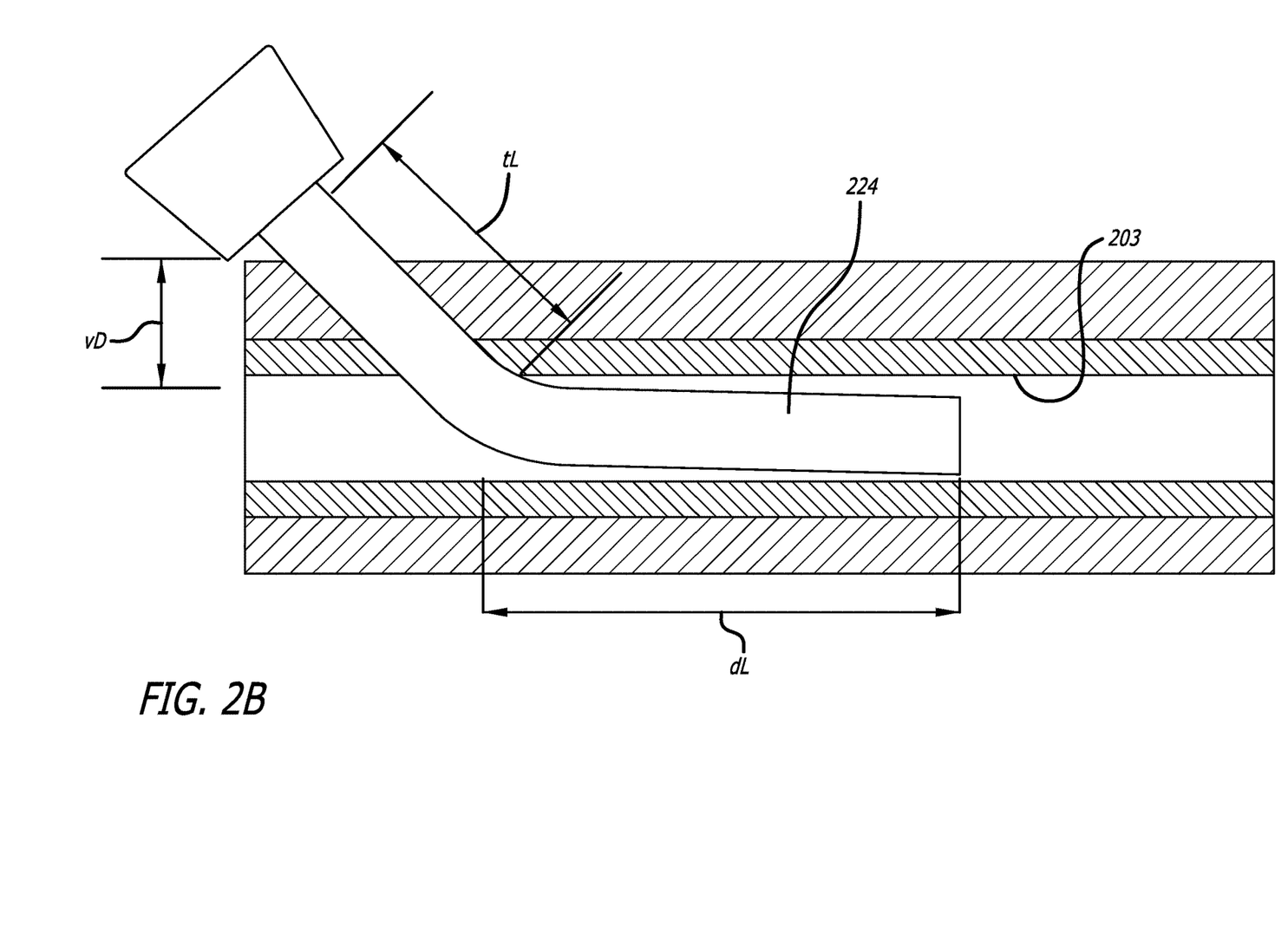
FIG. 2B illustrates a method of identifying catheters by the minimum catheter length tool, in accordance with some embodiments.

FIG. 2B illustrates a method of identifying catheters by the minimum catheter length tool, in accordance with some embodiments. In some embodiments, the minimum catheter length tool 110 may be configured to use various dimensions to identify catheters with overall catheter lengths that satisfy the desired minimum catheter dwell lengths in target vessels at various vessel depths. In some embodiments, the target blood vessel 203 has a vessel depth ("vD"). In some embodiments, a catheter 224 has a desired minimum catheter dwell length, ("dL"), and a travel length ("tL"), the length the catheter 224 travels to get to the target vessel at the specific angle of insertion. The minimum catheter length tool 110 will display only catheters that have a minimum overall catheter length of the desired minimum catheter dwell length, (dL)+the travel length (tL). For example, if a target vessel depth vD is 1.5 cm, the desired minimum catheter dwell length is 1.5 cm, the minimum catheter length tool 110 may be configured to calculate the travel length (tL) being 2.1 cm and will only display catheters that have a minimum overall catheter length of 3.6 cm. A catheter with a minimum overall catheter length of at least 3.6 cm is able to access a target vessel depth of 1.5 cm while allowing for least 1.5 cm of the catheter 224 to dwell in the target blood vessel 203.

Figure 3A:
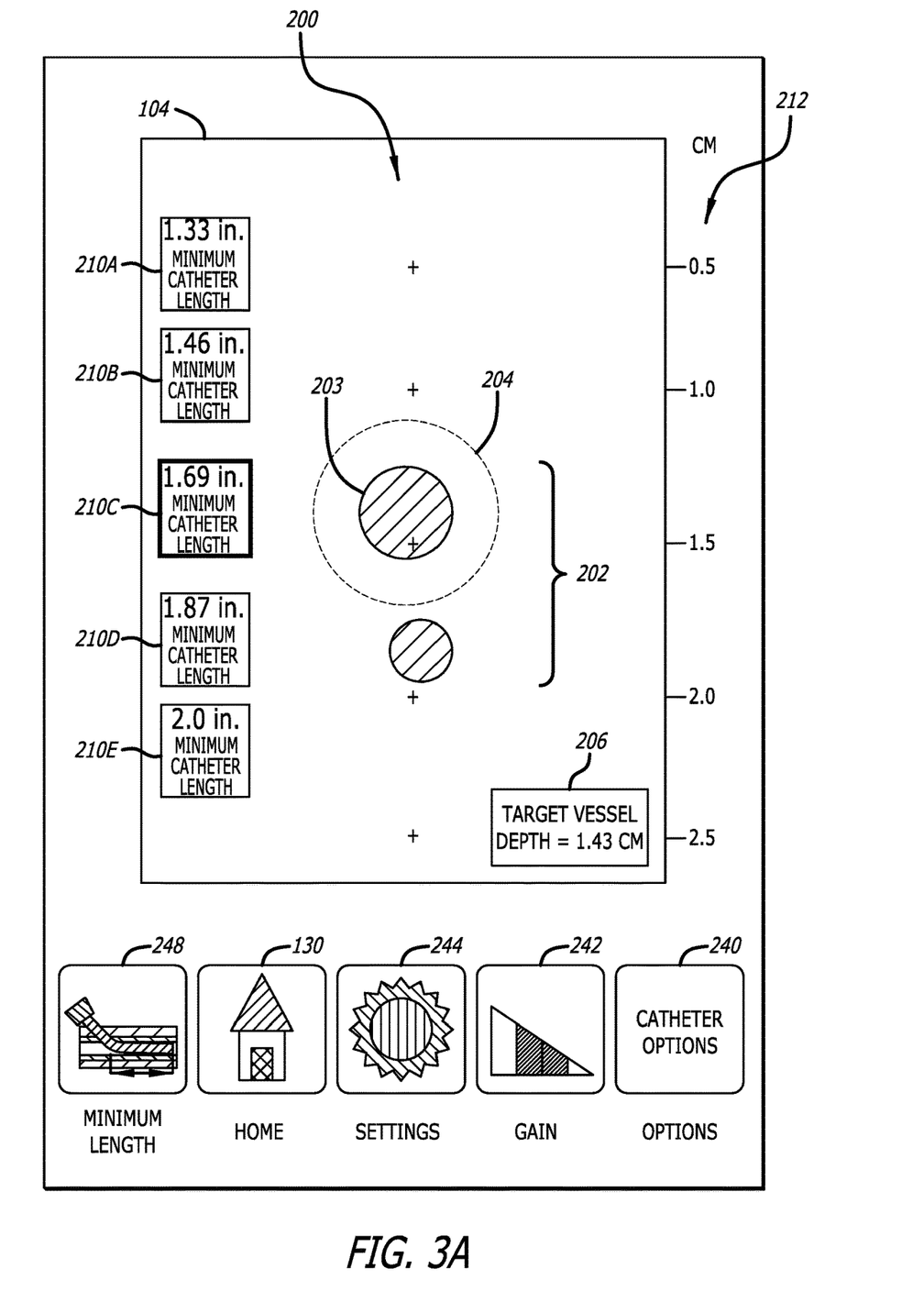
FIG. 3A illustrates a depiction of a display of various components of the minimum catheter length tool, in accordance with some embodiments.

FIG. 3A illustrates an ultrasound image screen 200 of the minimum catheter length tool 110, in accordance with some embodiments. In some embodiments, the ultrasound image screen 200 of the minimum catheter length tool 110 includes a dynamic ultrasound image of the one or more blood vessels 202. In some embodiments, the ultrasound image screen 200 includes a static ultrasound image of the one or more blood vessels 202. The ultrasound image screen 200 can include vessel depth indicators 212 displaying segmented depth markers to indicate a depth of a target blood vessel 203. The ultrasound image 200 includes a target vessel selector 204 used to select a target blood vessel 203 from the one or more blood vessel 202 on the display 104. Using the target vessel selector 204 identifies a specific target vessel 203 from the one or more blood vessels 202 displayed. The tool 110 can then display a depth of the selected target vessel 203 as indicated by the target vessel depth icon 206.

In some embodiments, the tool 110 can automatically determine a specified target vessel 203 from the one or more blood vessels 202 displayed. In an embodiment, a user can select a specified target vessel 203, e.g. by selecting the target vessel 203 on the touch screen display, manipulating a cursor on the display, or the like. In some embodiments, selecting the target blood vessel 203 using the vessel selector 204 will bring up the parameter input screen 112 of FIG. 2A. In some embodiments, selecting the minimum length icon 248 will bring up the parameter input screen 112 of FIG. 2A.

In some embodiments, the tool 110 may be configured to display a plurality of "minimum catheter length" icons 210A-E that depict the minimum catheter length needed to meet the minimum catheter dwell length in a vessel that resides at the respective vessel depth. The plurality of "minimum catheter length" icons 210A-E may be configured to correspond to the vessel depth indicators 212 depicted on the display. In some embodiments, one of the plurality of "minimum catheter length" icons 210C that corresponds with the targeted vessel depth as indicated by the vessel selector 204 may be configured to be highlighted. The user may select the highlighted "minimum catheter length" icon 210C which may be configured to transition the user to a catheter options user interface 220 that will be described more detail herein.

In an embodiment, one of the depth icons 206 or the length icons 210 may be displayed proximate the selected target vessel 203 and dynamically update as the target vessel selector 204 is moved about the display 104. In an embodiment, one of the depth icon 206 or the length icon 210 may be displayed proximate the target vessel 203 when the target vessel 203 is selected.

In an embodiment, the tool 110 may automatically navigate between different screens, e.g. the parameter input screen (FIG. 2A) or the ultrasound image screen (FIG. 3A) as the user selects different options, or as different inputs are required from the user. Optionally, the user can navigate between different screens using the arrows 128A/B or similar icons.

In some embodiments, the catheter options screen 220 may be selected by a "catheter options" icon 240. In some embodiments, the minimum catheter length tool 110 may include a "gain" icon 242 that may be configured to depict the strength of the received ultrasound signal. In some embodiments, the minimum catheter length tool 110 may include a "settings" icon 244 that may be configured to display and adjust the settings of all the components of the minimum length catheter tool 110. In some embodiments, the minimum catheter length tool 110 may include the "home" icon 130 configured to return the user to a home screen, the ultrasound image screen 200, or the like. It can be appreciated that other icons used in ultrasound imaging systems may be included.

Figure 3B:
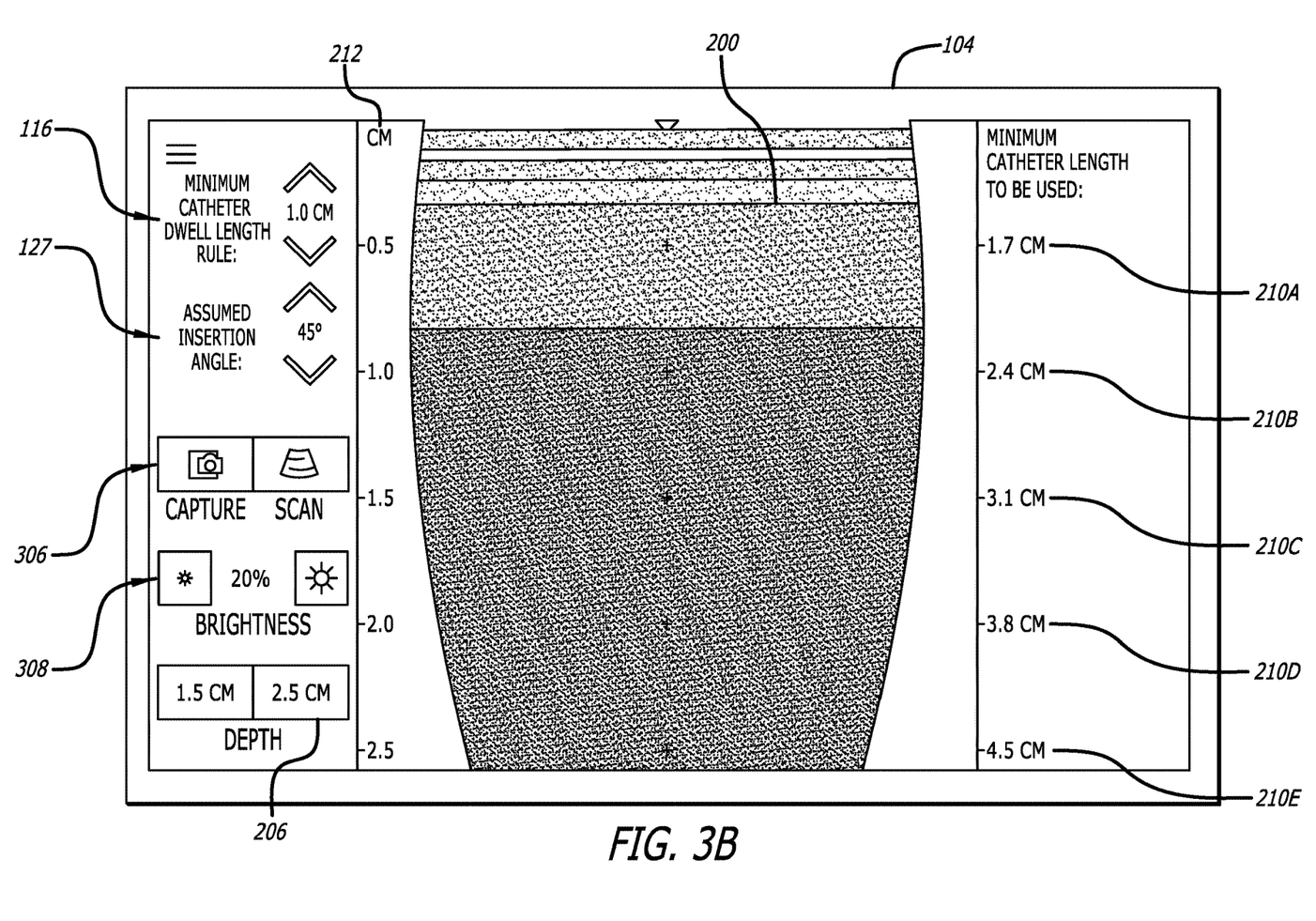
FIG. 3B illustrates an exemplary screenshot of an ultrasound imaging system including a minimum catheter length tool, in accordance with some embodiments.

FIG. 3B illustrates an exemplary screenshot of the ultrasound imaging system on the display 104 including the minimum catheter length tool 110, in accordance with some embodiments. In some embodiments, the tool 110 can be configured to display the ultrasound image 200 including an angle of insertion icon 127 and the minimum catheter dwell length indicator icon 116. The tool 110 can further be configured to display one or more of the plurality of "minimum catheter length" icons 210A-E, target vessel depth icon 206 or the vessel depth indicators 212 as previously described. The tool 110 may further be configured to display a display selection icon 306. In some embodiments, the display selection icon 306 may be configured to toggle between the static ultrasound image 200 and the dynamic ultrasound image 200. The tool 110 may be configured to display a display adjustment icon 308. In some embodiments, the display adjustment icon 308 may be configured to adjust the brightness of the display 104.

Figure 4:
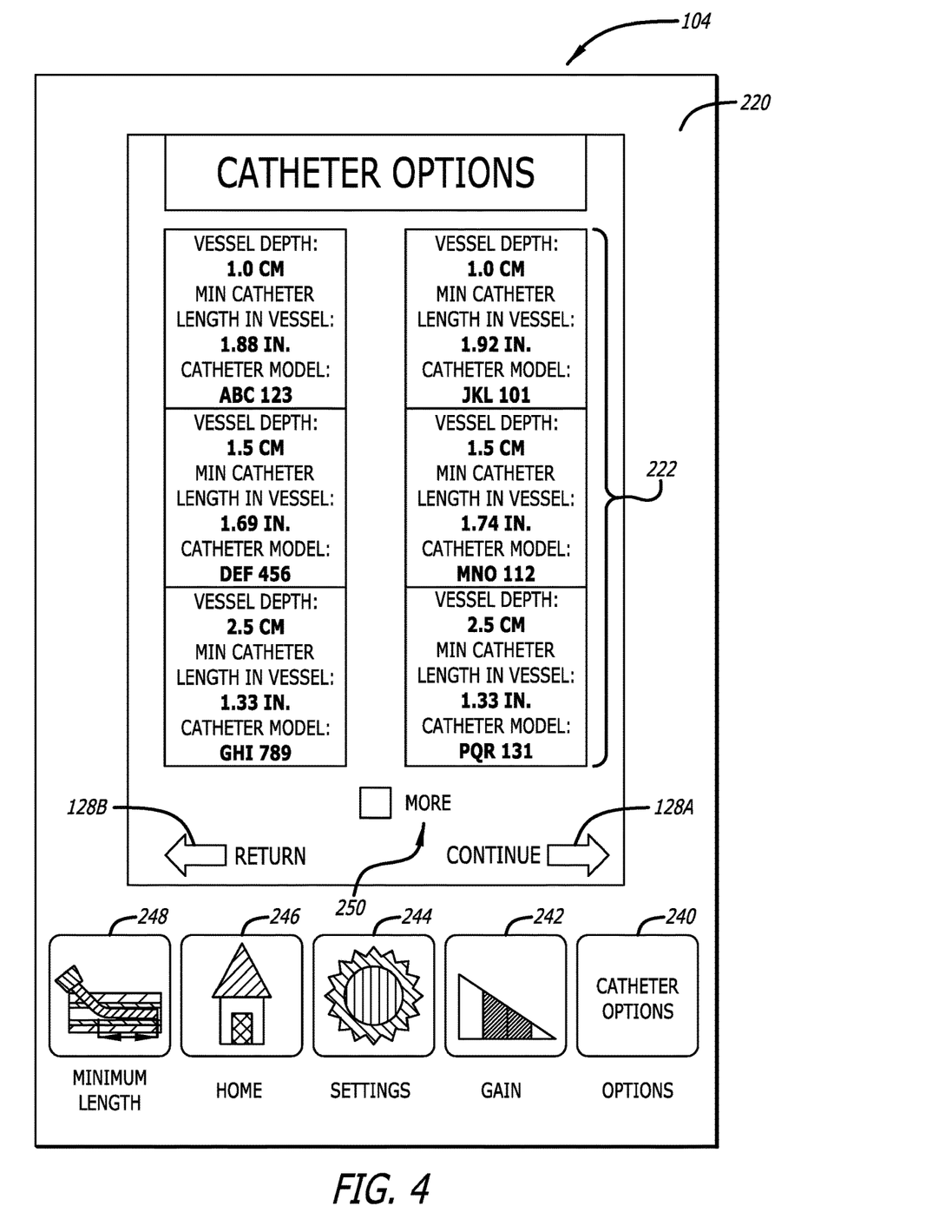
FIG. 4 illustrates various components of the minimum catheter length tool, in accordance with some embodiments.

FIG. 4. illustrates a catheter options screen 220 of the minimum catheter length tool on the display 104, in accordance with some embodiments. Based on the inputs and information provided from the parameter input screen (FIG. 2A) and the ultrasound image screen (FIG. 3A), the catheter options screen 220 can display, a selection of catheters 222 that can be used to access the target vessel 203. These catheters 222 fit the user selected criteria including catheter insertion angle and minimum catheter dwell length in target blood vessel when accessing the target blood vessel at the given depth. In some embodiments, each catheter option includes the specific information from the user selected criteria including one or more of the target vessel depth, the user selected minimum catheter length in the vessel or the catheter model. In some embodiments, selecting one of the catheter options may provide additional information, about the specific catheter including one of: catheter diameter, catheter cross sectional area, an indicator of whether the selected catheter will fit within the target blood vessel, vessel occupancy with that specific catheter, the procedures the catheter is used for, purchase price, current inventory, ordering information, combinations thereof, or the like. In some embodiments, the user can select additional catheter options not displayed on the catheter options user interface 220 or adjust the number of catheter options displayed on the catheter options user interface 220 by selecting a "more" icon 250. Additionally, in some embodiments, a plurality of icons may be depicted including one or more of the "minimum length" icon 248, the "home" icon 130, the "settings" icon 244, the "gain" icon 242 or the "catheter options" icon 240, as described herein.

Figure 5:
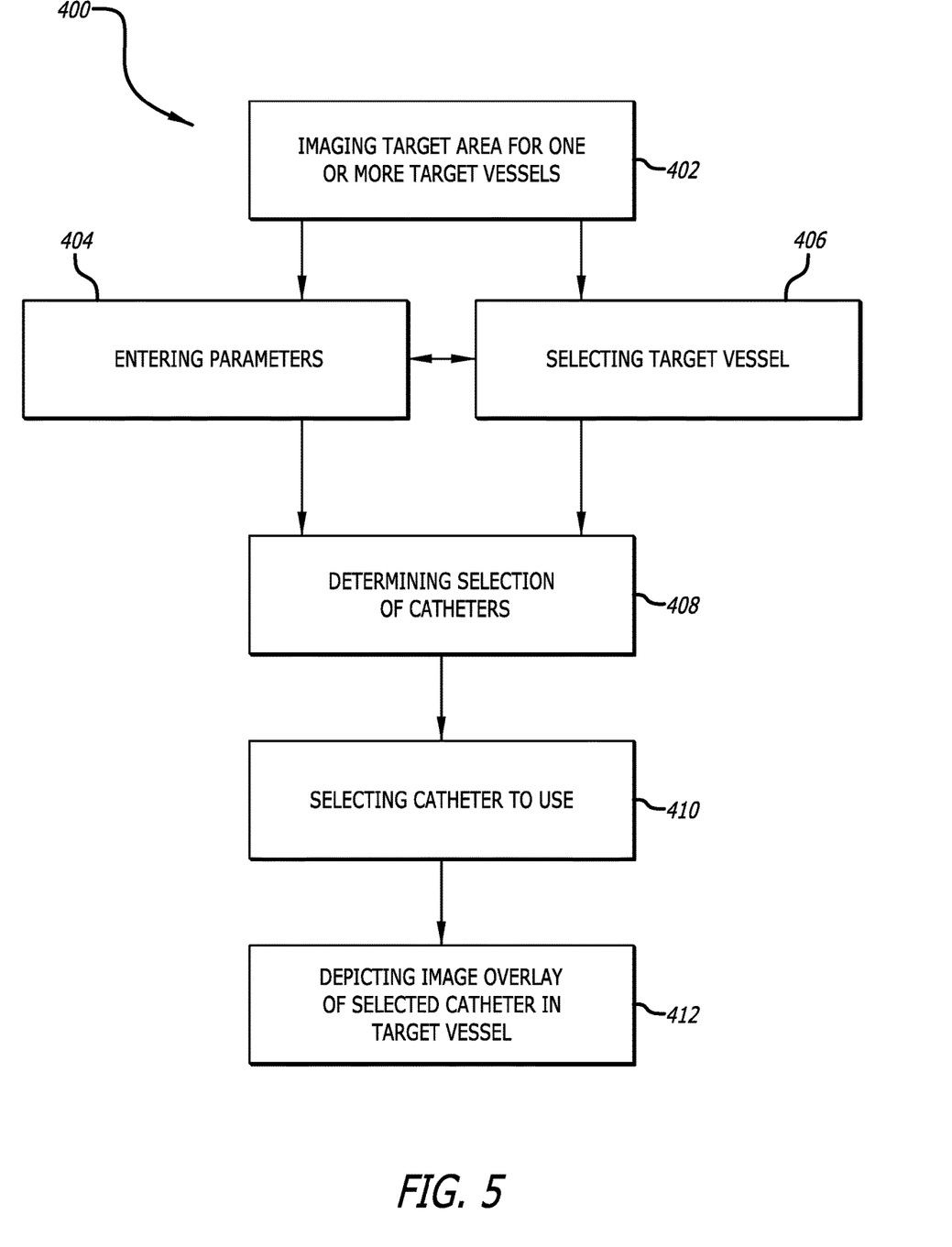
FIG. 5 illustrates a flow chart diagram of a method for selecting a vascular access device for accessing a target blood vessel, in accordance with some embodiments.

FIG. 5 illustrates a block diagram of a method for selecting a vascular access device for accessing a target blood vessel, in accordance with some embodiments. The method 400 includes imaging the target area for one or more blood vessels (block 402). In some embodiments, imaging including using an ultrasound imaging system 100 having a console 102 communicatively coupled to an ultrasound probe 106 and a display 104. In some embodiments, the console 102 may include a minimum catheter length tool 110. In some embodiments, the minimum catheter length tool 110 may be configured to receive user parameter input to determine a selection of catheters that may be capable of accessing a target blood vessel at the prescribed depth. The method 400 further includes entering parameters (block 404). In some embodiments, entering includes entering the angle of insertion and the minimum catheter dwell length as parameters to use for choosing a catheter. In some embodiments, entering including entering the angle of insertion and the minimum catheter dwell length on a parameter input screen 112. The method 400 includes selecting one or more target vessels (block 406). In some embodiments, selecting includes selecting using a target vessel selector 204 on an ultrasound image screen 200. The method 400 includes determining a selection of catheters 222 (block 408). In some embodiments, determining a selection of catheters includes using the minimum length catheter tool 110 to determine the selection of catheters 222 that are capable of accessing the target vessel 203 based up the angle of insertion, the target vessel depth and the minimum catheter dwell length. The method 400 includes selecting a catheter to use (block 410). In some embodiments, selecting the catheter to use includes selecting from the selection of catheters 222 generated by the minimum catheter length tool 110. The method 400 includes depicting ultrasound image overlay of selected catheter in target vessel (block 412). In some embodiments, the user can move between entering parameters (block 404) and selecting one or more target vessels (block 406) until the user is satisfied with the results.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound imaging system, comprising:
   an ultrasound probe designed to produce an ultrasound image including one or more blood vessels below a skin surface of a patient; and
   a console operably coupled to the ultrasound probe, comprising:
   a processor;
   a memory having instructions stored thereon that, when executed by the processor, cause operations of:
      generating a first display screen illustrating the ultrasound image and configured to receive user input selecting a blood vessel display in the ultrasound image,
      generating a second display screen different than the first display screen, the second display screen illustrating:
         a user selection element configured to receive first user input selecting an angle of insertion of a medical device within a target blood vessel,
         a graphical representation of the medical device at the selected angle of insertion, and
         a user input element configured to receive second user input increasing or decreasing a minimum dwell length of the medical device, wherein the graphical representation of the medical device visually represents the first user input and the second user input; and
      determining (i) a depth of the selected blood vessel, and (ii) a selection of medical devices that adhere to constraints based on a user selection of one or both of the minimum dwell length or the selected angle of insertion; and
   a third display configured to depict the ultrasound image, a user selected blood vessel, and a user selected medical device showing the user selection of one or both of the minimum dwell length or the selected angle of insertion.

2. The ultrasound imaging system according to claim 1, wherein the user selected medical device is a catheter, and wherein the selection of medical devices is a selection of catheters.

3. The ultrasound imaging system according to claim 2, wherein the instructions include logic, comprising:
   a parameter logic configured to receive one or both of the second user input indicating the minimum dwell length or the first user input selecting the angle of insertion;
   a target vessel selector logic configured to determine the depth of the selected blood vessel; and
   a catheter selection logic configured to provide the selection of catheters based on the depth of the selected blood vessel, the first user input, and the second user input.

4. The ultrasound imaging system according to claim 3, wherein the memory comprises a data store configured to store a list of catheters including information about a catheter length of each of the list of catheters.

5. The ultrasound imaging system according to claim 4, wherein the instructions further include a communications logic configured to update the list of catheters from a remote computing device.

6. The ultrasound imaging system according to claim 1, wherein the ultrasound probe is wirelessly coupled to the console.

7. The ultrasound imaging system according to claim 1, wherein the console includes a touch screen.

8. The ultrasound imaging system according to claim 1, wherein the second display screen receives both the first user input and the second user input.

* * * * *